(12) United States Patent
Miller (10) Patent No.: US 10,959,736 B2
(45) Date of Patent: *Mar. 30, 2021

(54) INFLATABLE ATRIAL APPENDAGE OCCLUSION APPARATUS AND METHODS

(71) Applicant: AtriCure, Inc., Mason, OH (US)

(72) Inventor: Kenneth Lance Miller, Hamilton, OH (US)

(73) Assignee: AtriCure, Inc., Mason, OH (US)

( * ) Notice: Subject to any disclaimer, the term of this patent is extended or adjusted under 35 U.S.C. 154(b) by 69 days.

This patent is subject to a terminal disclaimer.

(21) Appl. No.: 16/246,465

(22) Filed: Jan. 12, 2019

(65) Prior Publication Data

US 2019/0142434 A1    May 16, 2019

Related U.S. Application Data

(63) Continuation of application No. 15/046,183, filed on Feb. 17, 2016, now Pat. No. 10,182,823.

(51) Int. Cl.
*A61B 17/12* (2006.01)
*A61B 17/122* (2006.01)
*A61B 17/128* (2006.01)
*A61B 17/00* (2006.01)

(52) U.S. Cl.
CPC ...... *A61B 17/12136* (2013.01); *A61B 17/122* (2013.01); *A61B 17/12109* (2013.01); *A61B 17/1285* (2013.01); *A61B 17/12122* (2013.01); *A61B 2017/00557* (2013.01); *A61B 2017/1205* (2013.01)

(58) Field of Classification Search
CPC ............ A61B 17/122; A61B 17/12122; A61B 17/1285; A61B 2017/00557; A61B 2017/1205; A61B 17/12136; A61B 17/12113; A61B 17/12109; A61B 2017/22051

See application file for complete search history.

(56) References Cited

U.S. PATENT DOCUMENTS

| | | | |
|---|---|---|---|
| 3,538,917 A | 11/1970 | Selker | |
| 3,675,656 A | 7/1972 | Hakim | |
| 3,730,186 A | 5/1973 | Edmunds et al. | |
| 4,587,955 A | 5/1986 | Gengler | |
| 4,708,140 A | 11/1987 | Baron | |
| 4,800,879 A | 1/1989 | Golyakhovsky | |
| 4,881,939 A | 11/1989 | Newman | |
| 5,074,869 A * | 12/1991 | Daicoff | A61B 17/12 606/158 |

(Continued)

FOREIGN PATENT DOCUMENTS

| DE | 0319261 | 7/1918 |
|---|---|---|
| EP | 0611561 | 8/1994 |

(Continued)

OTHER PUBLICATIONS

PCT International Search and Written Opinion dated Nov. 8, 2016 for PCT App. Ser. No. PCT/US2016/033661.

*Primary Examiner* — Katrina M Stransky
(74) *Attorney, Agent, or Firm* — Henricks Slavin LLP (57) ABSTRACT

An atrial appendage occlusion apparatus including an inflatable body defining a compression region that is sized and shaped to receive an atrial appendage and a self-sealing valve associated with the inflatable body.

18 Claims, 5 Drawing Sheets

(56)  References Cited

U.S. PATENT DOCUMENTS

| | | | |
|---|---|---|---|
| 5,201,758 | A | 4/1993 | Glover |
| 5,454,826 | A | 10/1995 | Ueda |
| 6,067,991 | A | 5/2000 | Forsell |
| 8,636,754 | B2 | 1/2014 | Hughett, Sr. et al. |
| 8,753,363 | B2 | 6/2014 | Anderson et al. |
| 8,852,218 | B2 | 10/2014 | Hughett, Sr. et al. |
| 9,017,349 | B2 | 4/2015 | Privitera et al. |
| 9,737,309 | B1 * | 8/2017 | Ad .................. A61B 17/128 |
| 10,182,823 | B2 * | 1/2019 | Miller ............. A61B 17/12109 |
| 2004/0138684 | A1 | 7/2004 | Eton |
| 2005/0288706 | A1 | 12/2005 | Widomski |
| 2007/0173928 | A1 | 7/2007 | Morsi |
| 2013/0006343 | A1 | 1/2013 | Kassab |
| 2015/0250482 | A1 | 9/2015 | Slaughter et al. |

FOREIGN PATENT DOCUMENTS

| | | |
|---|---|---|
| WO | WO 2004064648 | 8/2004 |
| WO | WO 2014031903 | 2/2014 |
| WO | WO 2015164836 | 10/2015 |

\* cited by examiner

INFLATABLE ATRIAL APPENDAGE OCCLUSION APPARATUS AND METHODS

CROSS-REFERENCE TO RELATED APPLICATIONS

This application is a continuation of application Ser. No. 15/046,183, filed Feb. 17, 2016, now U.S. Pat. No. 10,182,823.

BACKGROUND

1. Field

The present disclosure relates generally to the occlusion of atrial appendages and other anatomic structures.

2. Description of the Related Art

Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. The wavelets (called "reentry circuits") disrupt the normally uniform activation of the left and right atria. Because of a loss of atrioventricular synchrony, the people who suffer from atrial fibrillation also suffer the consequences of impaired hemodynamics and loss of cardiac efficiency. They are also at much greater risk of strokes and other thromboembolic complications because of loss of effective contraction and atrial stasis. With respect to strokes, thrombus can form in left atrial appendage, break off, and cause a stroke. The risk of stroke for people with atrial fibrillation is about five (5) times that of those who do not have atrial fibrillation.

A variety of atrial appendage occlusion apparatus and methods have been proposed, including those illustrated and described in U.S. Pat. No. 9,017,349, which is incorporated herein by reference in its entirety. Although such apparatus and methods have proven to be a significant advance in the art, the present inventor has determined that atrial appendage occlusion apparatus and methods are susceptible to improvement.

SUMMARY

An atrial appendage occlusion apparatus in accordance with one implementation of a present invention includes an inflatable body defining a compression region that is sized and shaped to receive the atrial appendage and a self-sealing valve associated with the inflatable body.

An atrial appendage occlusion apparatus in accordance with one implementation of a present invention includes a self-sealing valve and means, operably connected to the self-sealing valve, for applying a compression pressure to the atrial appendage that is sufficient to occlude the atrial appendage in response to a receipt of fluid by way of the self-sealing valve.

An method in accordance with one implementation of a present invention includes the step of occluding an atrial appendage by applying a compression pressure to the exterior surface of the atrial appendage with an inflatable apparatus.

There are a number of benefits associated with the present appendage occlusion apparatus and methods. By way of example, but not limitation, the present occlusion apparatus is atraumatic and are less likely to damage tissue or tear the atrial appendage, which can lead to excessive blood loss, than conventional apparatus. The present occlusion apparatus may be compressed to a size that is smaller than its final size and, therefore, can be deployed through a smaller incision than conventional occlusion apparatus. The devices that deploy the present occlusion apparatus may be smaller and less complex than those which must be capable of spreading conventional occlusion apparatus that are biased to a closed state. The present occlusion apparatus also lack springs and other mechanical components that can hinder deployment. With respect to manufacturing, the present occlusion apparatus may be formed through the use of relatively simple molding processes.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

One example of an inflatable atrial appendage occlusion apparatus (or "occlusion apparatus") in accordance with at least one of the present inventions is generally represented by reference numeral 100 in FIGS. 1-4. The exemplary occlusion apparatus 100, which is shown in an uninflated state in FIGS. 1-4, includes an inflatable body 102, with an inner surface 104 that defines and surrounds an open compression region 106, and may include a valve 108 that closes after the inflatable body 102 has been inflated with a fluid (i.e., a liquid or a gas). The exemplary inflatable body 102 may have a pair of elongate linear hollow tubes 110 and a pair of semi-circular hollow end tubes 112 that connect the linear tubes to one another. The tubes 110 and 112 together define an interior volume 114 that extends around the compression region 106. The tubes 110 and 112 may also be circular in cross-section, and the exemplary inflatable body 102 defines an elongated torus shape. As such, the width of the compression region 106 (i.e., the horizontal dimension in FIG. 4) varies over its height (i.e., the vertical dimension in FIG. 4). Other cross-sectional shapes are discussed below with reference to FIGS. 10-12.

The exemplary occlusion apparatus 100 may also include support members 116 that prevent the inflatable body 102 from bulging outwardly when the occlusion apparatus is inflated around an atrial appendage, or other anatomical structure, that is located within the compression region 106. The support members 116 may be relatively stiff, i.e., stiffer than the inflation body, and extend along the outer surfaces 118 of the linear hollow tubes 110. So configured and arranged the support members 116 may add stiffness to portions of the hollow tubes 110 opposite the compression region 106 and focuses the expansion of the tubes 110 inwardly into the compression region during inflation. In the embodiment illustrated in FIGS. 1-4, the support members 116 are semi-circular and cover approximately one-half of the circumferences of the hollow tubes 110 in a plane perpendicular to the longitudinal axis A-A. The lengths of the exemplary support members 116 may also be the same as (or close to) the lengths of the hollow tubes 110. The support members 116 may be shorter than the hollow tubes 110 in other implementations.

Figure 1:
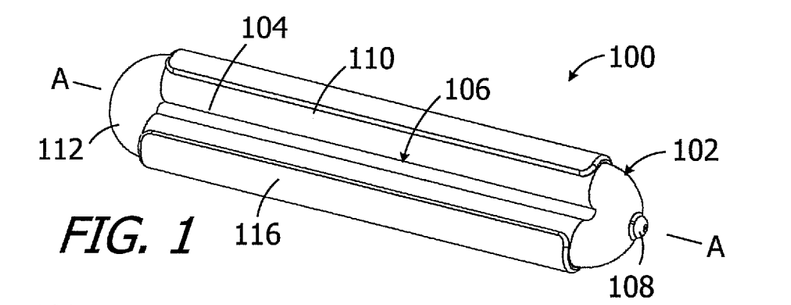
FIG. 1 is a perspective view of an inflatable atrial appendage occlusion apparatus in accordance with one embodiment of a present invention.
Figure 2:
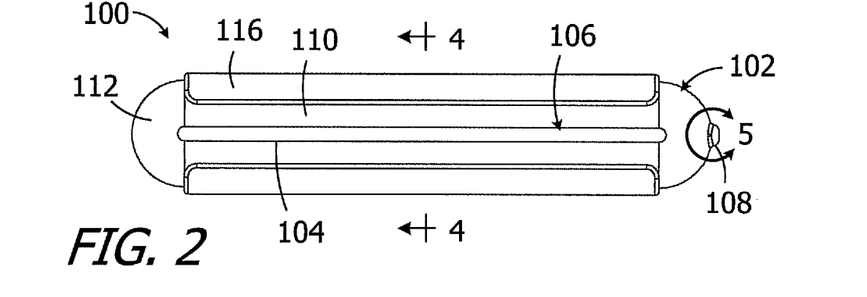
FIG. 2 is a plan view of the inflatable atrial appendage occlusion apparatus illustrated in FIG. 1.
Figure 3:
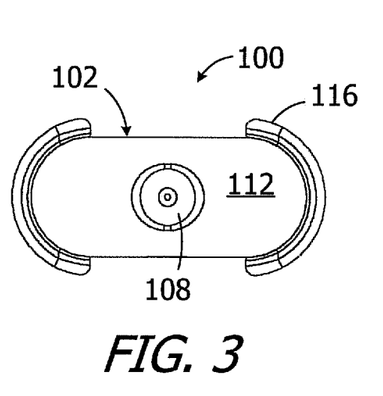
FIG. 3 is an end view of the inflatable atrial appendage occlusion apparatus illustrated in FIG. 1.
Figure 4:
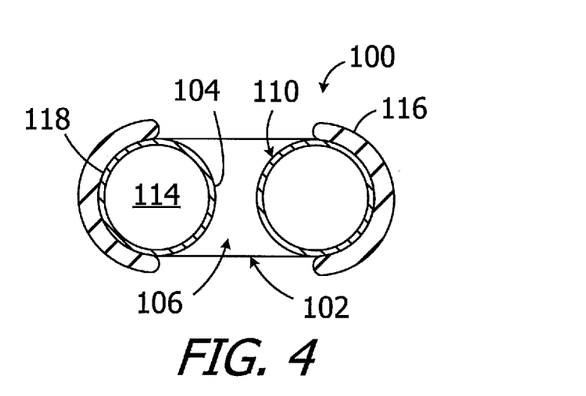
FIG. 4 is a section view taken along line 4-4 in FIG. 1.
Figure 5:
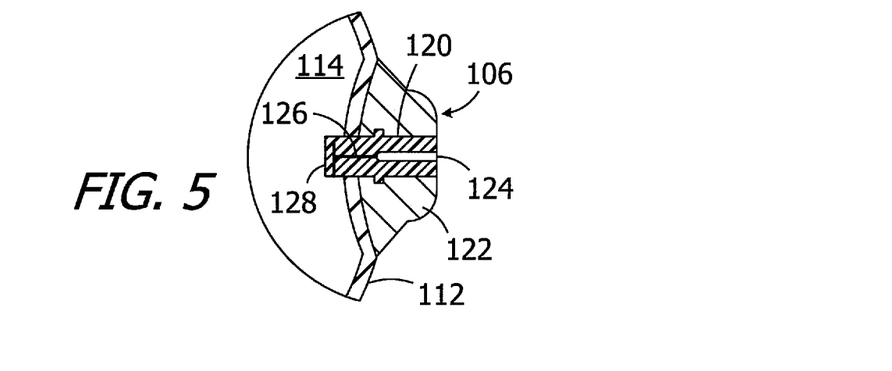
FIG. 5 is an enlarged section view of a portion of FIG. 2.

Turning to FIG. 5, the exemplary valve 108 may be a self-sealing valve that allows the inflatable body 102 to be inflated in situ, after the occlusion apparatus 100 has been positioned around an atrial appendage in the manner described below with reference to FIGS. 18-21, and then remain inflated after the deployment process is complete. Although the present inventions are not limited to any particular valve, the exemplary valve 108 includes may include a plug 120 and a base 122. The plug 120 may extend through the base 122 and the inflatable body end tube 112 and into the interior volume 114. The plug 120 may have a receptacle 124, a narrow slit 126 and a flap 128 that covers the end of the narrow slit. The narrow slit 126 and flap 128 may be biased to the closed state illustrated in FIG. 5 to prevent fluid within the inflatable body interior volume 114 from escaping. During the inflation process, a needle or other inflation tool may be inserted into the receptacle 124, and pushed through the narrow slit 126 until the flap 128 opens. Fluid may be injected into the interior volume 114 by way of the inflation tool and the opened valve 108. The valve 108 may return to the closed state to which it is biased when the inflation tool is removed.

Figure 6:
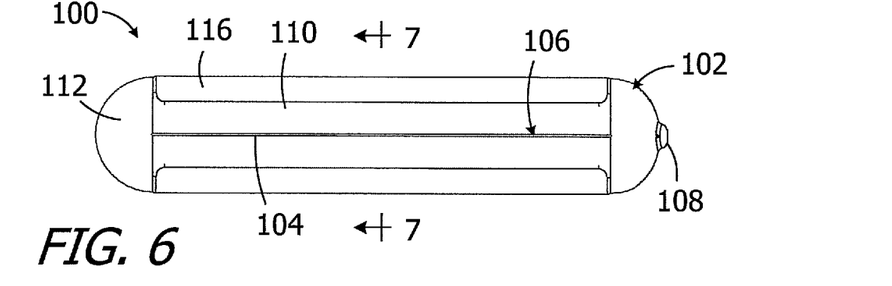
FIG. 6 is a plan view of the inflatable atrial appendage occlusion apparatus illustrated in FIGS. 1-5 in an inflated state.
Figure 7:
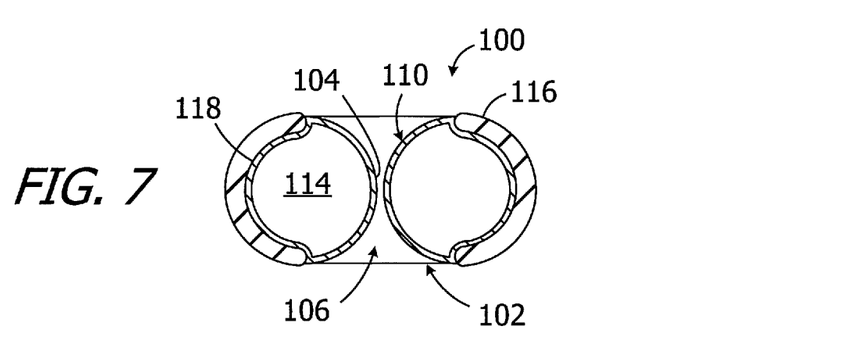
FIG. 7 is a section view taken along line 7-7 in FIG. 6.

Referring to FIGS. 6 and 7, inflation of the inflatable body 102 reduces the distance between the hollow tubes 110 and, accordingly, reduces the size of the compression region 106. As a result, the inflated hollow tubes 110 may compress and occlude an atrial appendage in the manner describe below with reference to FIGS. 18-21. The support members 116 do not deflect when the inflatable body 102 is inflated, and hold their shape in the manner illustrated in FIGS. 6 and 7.

With respect to materials and dimensions of an occlusion apparatus 100 configured to an atrial appendage, suitable materials for the inflatable body 102 may include, but are not limited to, thermoplastic elastomers (such as PET, Nylon, polyurethane, silicone, latex, Pebax™ and EVA) and bio-absorbable materials as well as fabric formed from natural fibers, synthetic fibers or artificial fibers (e.g., PVC fibers) that is covered with a polymer film (such as rubber film or polyurethane film), which may ensure gas and liquid impermeability. Suitable materials for the support members 116 may include, but are not limited to, bio-absorbable polymers (such as polylactides and glycolide compositions), organic synthetic polymers (such as polyethylene, polypropylene, Teflon, and polyurethanes), implantable polymers (such as PEEK), thermoplastic polymers (such as ABS, styrene, polycarbonate, Ultem™ and Celcon™), urethanes, and metals (such as stainless steel and titanium). In the exemplary context of the left atrial appendage occlusion, the length (along the longitudinal axis A-A) of the inflatable body 102 may range from 30 to 90 mm, the length of the compression region 106 may range from 20 mm to 60 mm, the uninflated width (perpendicular to the longitudinal axis A-A) of the compression region 106 at its narrowest point may range from 5 mm to 20 mm, the inflated width of the compression region 106 at its narrowest point may range from 0 to 1 mm, and the diameter of the elongate linear hollow tubes 110 may range from 1 mm to 6 mm when deflated and from 2 mm to 10 mm when inflated. However, other sizes may be contemplated for occlusion of other anatomical structures.

Figure 8:
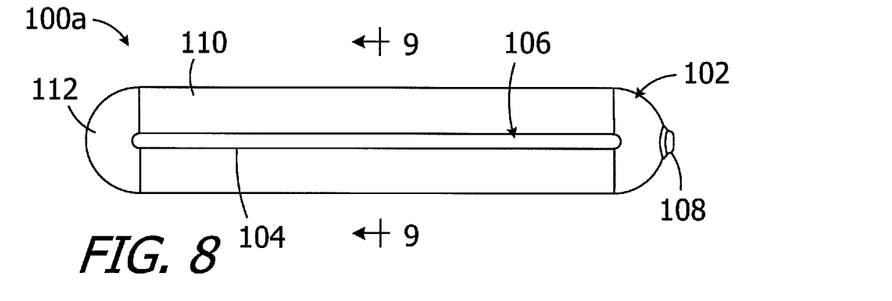
FIG. 8 is a plan view of an inflatable atrial appendage occlusion apparatus in accordance with one embodiment of a present invention.
Figure 9:
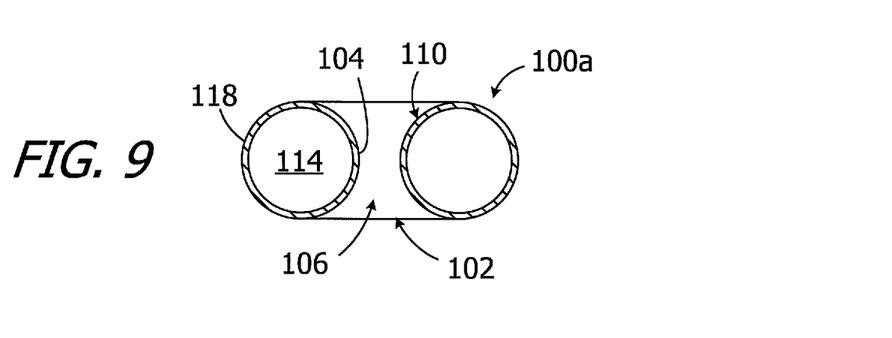
FIG. 9 is a section view taken along line 9-9 in FIG. 8.

The present inflatable atrial appendage occlusion apparatus may be susceptible to a wide variety of variation. By way of example, but not limitation, the exemplary occlusion apparatus 100a illustrated in FIGS. 8 and 9 is essentially identical to occlusion apparatus 100 and similar elements are represented by similar reference numerals. However, the support members 116 have been omitted. The support members may be omitted when, for example, the properties of material used to form the inflatable body 102 (e.g., the type and/or thickness of the material) results in an occlusion apparatus that is sufficiently stiff, absent the support members, to occlude the atrial appendage when inflated.

Figure 10:
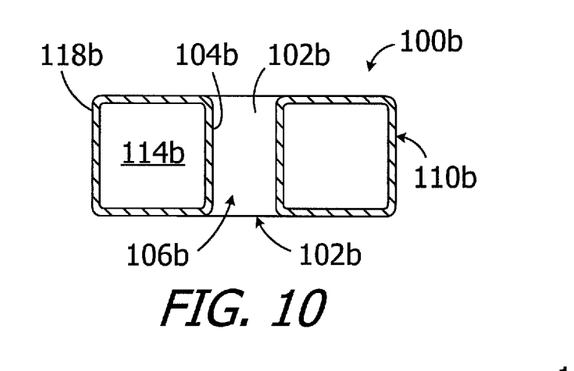
FIG. 10 is a section view of an inflatable atrial appendage occlusion apparatus in accordance with one embodiment of a present invention.
Figure 11:
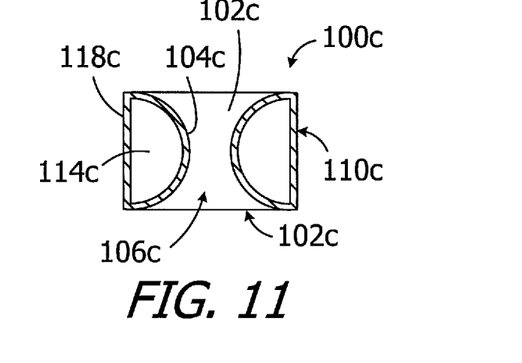
FIG. 11 is a section view of an inflatable atrial appendage occlusion apparatus in accordance with one embodiment of a present invention.

The present inflatable atrial appendage occlusion apparatus may not be limited to inflatable bodies with circular cross-sections. By way of example, but not limitation, the exemplary occlusion apparatus 100b illustrated in FIG. 10 is substantially similar to occlusion apparatus 100a and similar elements are represented by similar reference numerals. Here, however, the inflatable body 102b may include elongate linear hollow tubes 110b and an interior volume 114b that are rectangular (e.g., square) in cross-section. The end tubes 112b may have similar cross-sections. The inner and outer surfaces 104b and 118b are planar and the width of the compression region 106b is constant. Another exemplary occlusion apparatus is generally represented by reference numeral 100c in FIG. 11. Occlusion apparatus 100c is substantially similar to occlusion apparatus 100a and similar elements are represented by similar reference numerals. Here, however, the inflatable body 102c includes elongate linear hollow tubes 110c and an interior volume 114c that are semi-circular in cross-section. The end tubes 112c may have similar cross-sections. The inner surface 104b is curved, such that the width of the compression region 106c varies, while the outer surface 118c is planar.

Figure 12:
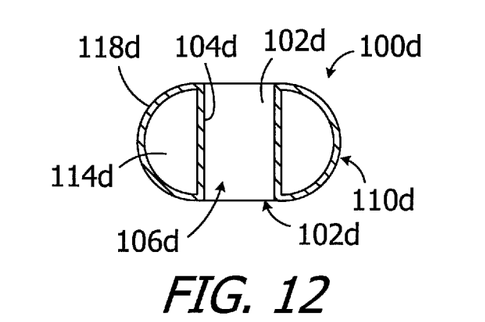
FIG. 12 is a section view of an inflatable atrial appendage occlusion apparatus in accordance with one embodiment of a present invention.

Turning to FIG. 12, the exemplary occlusion apparatus 100d is substantially similar to occlusion apparatus 100a and similar elements are represented by similar reference numerals. Here, however, the inflatable body 102d may include elongate linear hollow tubes 110d and an interior volume 114d that are semi-circular in cross-section. The end tubes 112d may have similar cross-sections. The inner surface 104b may be planar, such that the width of the compression region 106d is constant, while the outer surface 118d may be curved.

It should also be noted that the present inflatable bodies are not limited to those described above. Other cross-sectional shapes (e.g. elliptical and triangular shapes) may be employed. The respective sizes of the elongate linear hollow tubes (as evidenced by diameter, circumference or any other measurement) in an occlusion apparatus may be the same, as is illustrated in FIGS. 1-12, or may be different. The elongate linear hollow tubes may be parallel to one another (as shown) or non-parallel. Inflatable bodies that have non-inflatable end members that connect the elongate linear hollow tubes to one another may be provided. Here, each elongate linear hollow tube may have its own valve and will be separately inflated and, in at least some instances, simultaneously inflated by way of separate valves. In still other implementations, a solid non-inflatable bar may replace one of the elongate linear hollow tubes. The occlusion apparatus with non-circular hollow tubes may also be provided with support members, such as differently shaped versions of the support members 116 described above or the other support members described below.

Figure 13:
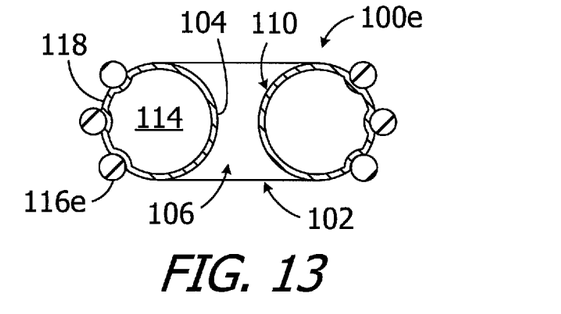
FIG. 13 is a section view of an inflatable atrial appendage occlusion apparatus in accordance with one embodiment of a present invention.

Turning to FIG. 13, the present support members (if employed) may not limited to the configuration illustrated in FIGS. 1-7. By way of example, but not limitation, the exemplary occlusion apparatus 100e as illustrated in FIG. 13 is essentially identical to occlusion apparatus 100 and similar elements are represented by similar reference numerals. However, the semi-circular support members 116 that extend around all or most of the outer surface 118 (note FIGS. 3 and 4) may be replaced by one or more rod-like support members 116e that each occupy a relatively small portion of the outer surface 118. Three bar-like support members 116e, which extend the entire lengths of the hollow tubes 110, are provided on the occlusion apparatus 100e. Although the illustrated bar-like support members 116e are solid and circular in cross-section, hollow and/or non-circular bar-like support members may be provided, as many bar-like support members that may extend along a portion of the length of the associated hollow linear tubes.

Figure 14:
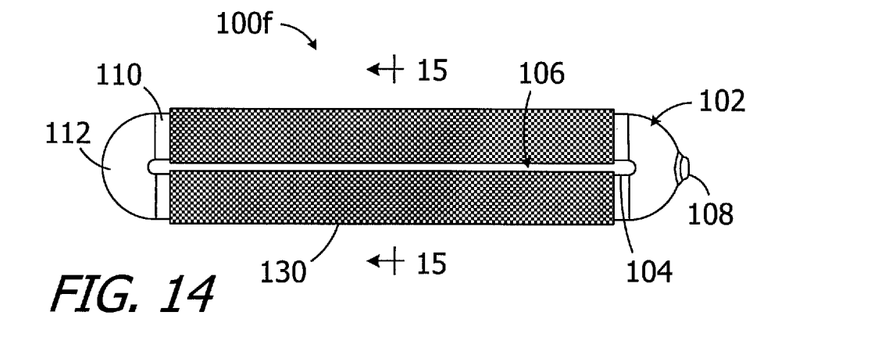
FIG. 14 is a plan view of an inflatable atrial appendage occlusion apparatus in accordance with one embodiment of a present invention.

The present inflatable atrial appendage occlusion apparatus may also include tissue in-growth material that will reduce the likelihood that the occlusion apparatus will slip off of the associated atrial appendage. Although not limited to any particular in-growth material or manner in which the material is carried by the inflatable body, one exemplary tissue in-growth material is a warp-knit polyester fabric material. As illustrated for example in FIGS. 14 and 15, one exemplary occlusion apparatus with tissue ingrowth material is generally represented by reference numeral 100f. The exemplary occlusion apparatus 100f is essentially identical to occlusion apparatus 100a and similar elements are represented by similar reference numerals. Here, however, the elongate linear hollow tubes 110 may be covered by tubes 130 formed from tissue in-growth material. In other embodiments, the tissue in-growth material may also cover the end tubes 112. It should also be noted that the tissue in-growth material may be added to any of the other atrial appendage occlusion apparatus described herein. Other materials that may be applied to the atrial appendage occlusion apparatus described herein include, but are not limited to, lubricious coatings (both hydrophilic and hydrophobic), abrasion and puncture-resistant coatings, tacky or high-friction coatings, electrically conductive coatings, antithrombogenic coatings, drug-release coatings, reflective coatings, and selective coatings.

Figures 15, 16:
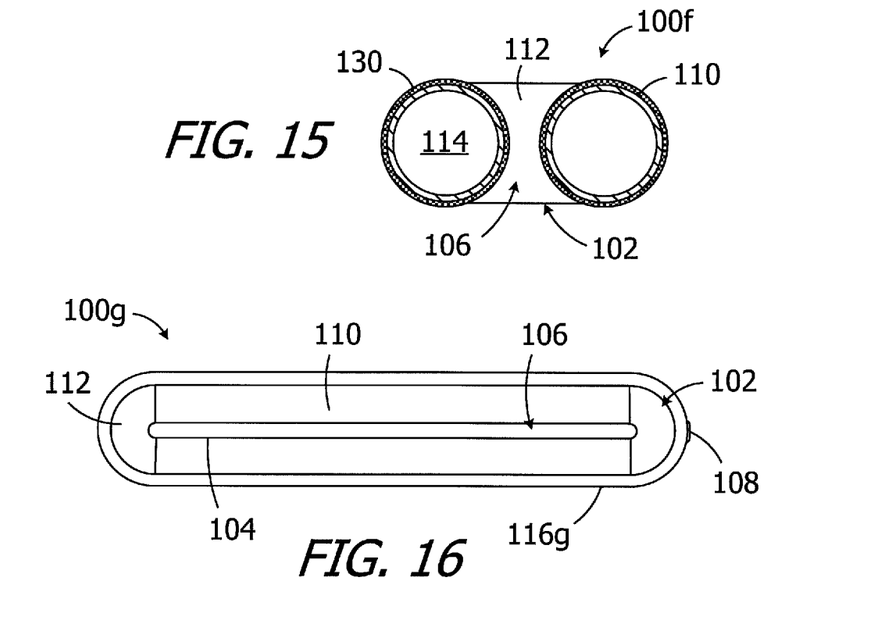
FIG. 15 is a section view taken along line 15-15 in FIG. 14.
FIG. 16 is a plan view of an inflatable atrial appendage occlusion apparatus in accordance with one embodiment of a present invention.
Figure 17:
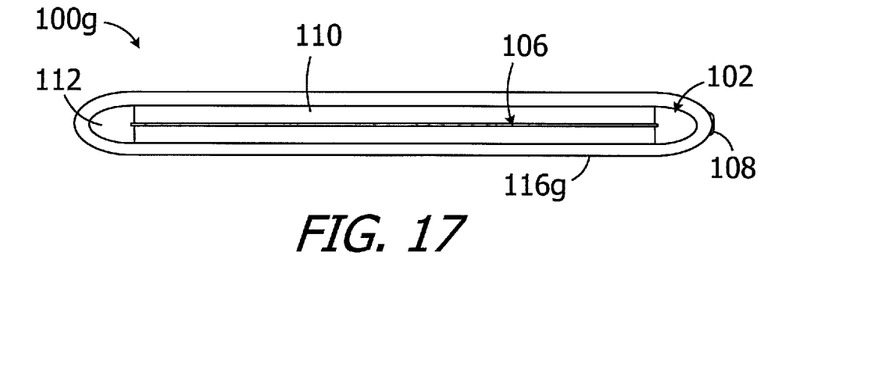
FIG. 17 is a plan view of the inflatable atrial appendage occlusion apparatus illustrated in FIG. 16 in a compressed state.

The exemplary inflatable atrial appendage occlusion apparatus 100g illustrated in FIGS. 16 and 17, which is otherwise identical to the occlusion apparatus 100, may include a support member 116g that extends completely around the outer perimeter (in the orientation illustrated in FIG. 16) of the inflatable body 102. As such, the support member 116g may cover portions of the semi-circular hollow end tubes 112 in addition to covering portions of the elongate linear hollow tubes 110. Alternatively, the support member 116g may cover only a portion of the outer perimeter of the inflatable body 102. In addition to preventing the inflatable body 102 from bulging outwardly when the occlusion apparatus 100g is inflated around an atrial appendage, or other anatomical structure, that is located within the compression region 106, the support member 116g is collapsible (note FIG. 17) and is biased to the open state illustrated in FIG. 16. The occlusion apparatus 100g may be compressed for insertion into the patient, and may return to the desired shape and size when the compression force is removed so that the inflatable body 102 can be positioned over the atrial appendage when inflated.

The inflatable atrial appendage occlusion apparatus described above may be deployed in any manner that results in the inflatable body being positioned over an atrial appendage and inflated to such an extent that the atrial appendage is occluded, i.e., to such an extent that the volume within the atrial appendage is isolated from the left atrium. By way of example, but not limitation, the present inflatable atrial appendage occlusion apparatus may be deployed through use devices, which that have been previously used to deploy atrial appendage occlusion clips. These devices may be modified to also inflate the present inflatable occlusion apparatus. Examples of such deployment devices are presented in U.S. Pat. No. 9,017,349, which is incorporated by reference in its entirety. Additional deployment devices examples are sold by AtriCure, Inc.

One example of an inflatable atrial appendage occlusion apparatus deployment method is illustrated in FIGS. 18-21.

The method may be performed with the exemplary deployment device 200, with any other suitable deployment device, or by hand. The exemplary deployment device 200 may include a deployment loop 202, a shaft 204 that is connected to a handle (not shown) and to the deployment loop by articulation joints 206, and suture ties 208 that temporarily connect the occlusion apparatus (here, occlusion apparatus 100) to the deployment loop. The exemplary deployment device 200 may also include a needle or other inflation tool 210 (FIG. 20) that, prior to the onset of the deployment procedure, is inserted into the occlusion device valve 108 to such an extent that the valve is held open by the inflation tool. The needle 210 may be connected to a fluid source (not shown), such as a syringe, by a tube 212 that is movable (with the needle) relative to the deployment loop 202 and shaft 204.

Figure 18:
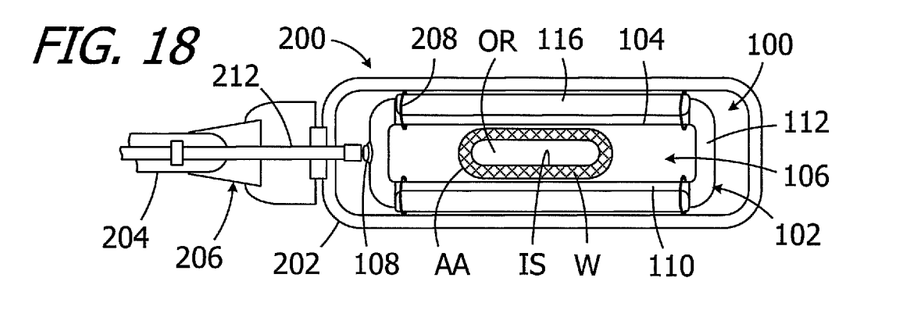
FIG. 18 is a plan, partial section view showing a portion of an inflatable atrial appendage occlusion apparatus deployment method in accordance with one embodiment of a present invention.

Referring more specifically to FIG. 18, the deployment device 200 may be used position the deflated inflatable body 102 of the occlusion device 100 over and around a non-occluded atrial appendage AA such that the atrial appendage may be located within the compression region 106. The occlusion device 100 may also be on or near the epicardial surface of the left atrium. If necessary, the atrial appendage AA may be manipulated into place with a separate, atraumatic tool. Prior to inflation, the inner surfaces IS of the atrial appendage walls W may be spaced apart from one another, which may define an open region OR that is in fluid communication with the left atrium.

Figure 19:
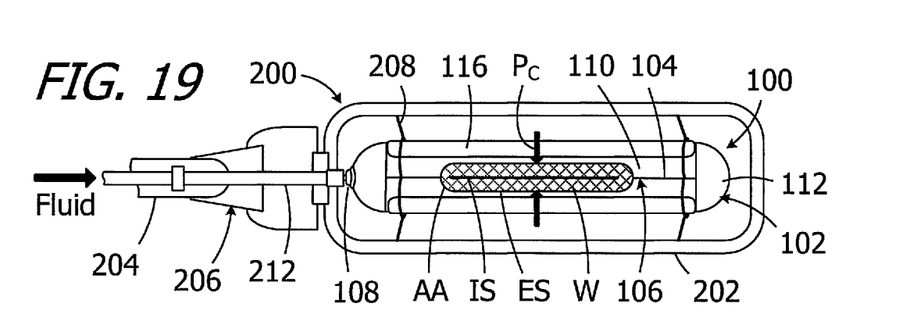
FIG. 19 is a plan, partial section view showing another portion of the inflatable atrial appendage occlusion apparatus deployment method.

Next, as illustrated for example in FIG. 19, the inflatable body 102 may be inflated with fluid that enters the interior volume 114 (FIG. 4) by way of the valve 108, needle 210 and tube 212. Suitable inflation fluids include, but are not limited to, air, inert gases, saline, substances that solidify at body temperature, and medical epoxy. Inflation of the inflatable body 102 may cause the elongate linear hollow tubes 110 to expand inwardly (note also FIG. 7). Thereby distance between the inner surfaces 104 and the size of the compression region 106 may be reduced, which may apply a compression pressure $P_C$ to exterior surface ES of the atrial appendage walls W. Put another way, the inflatable body 102 may perform the function of applying a compression pressure to the atrial appendage in response to the receipt of fluid through the valve 108. The compression pressure $P_C$ on the walls W, which may range from 0.2 to 100 psi, may be sufficient to force the inner surfaces IS into contact with one another, thereby occluding the atrial appendage and isolating the atrial appendage AA from the left atrium. Portions of the elongate linear hollow tubes 110 may be aligned with the atrial appendage AA may, as they do in the illustrated embodiment, deflect to accommodate the atrial appendage.

It should be noted here that, in some instances, the occlusion device 100 may not be in the desired location after inflation and repositioning of the occlusion device may be necessary. Because the inflation tool 210 may be located within the valve 108, thereby maintaining the valve in the open state, fluid may be removed from the inflatable body 102 by way of the inflation tool and tube 210. The inflatable body 102 may be re-inflated after the occlusion device 100 has been repositioned.

Figure 20:
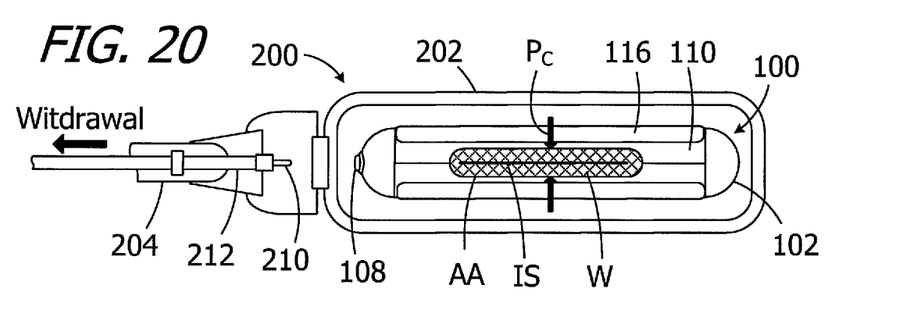
FIG. 20 is a plan, partial section view showing another portion of the inflatable atrial appendage occlusion apparatus deployment method.
Figure 21:
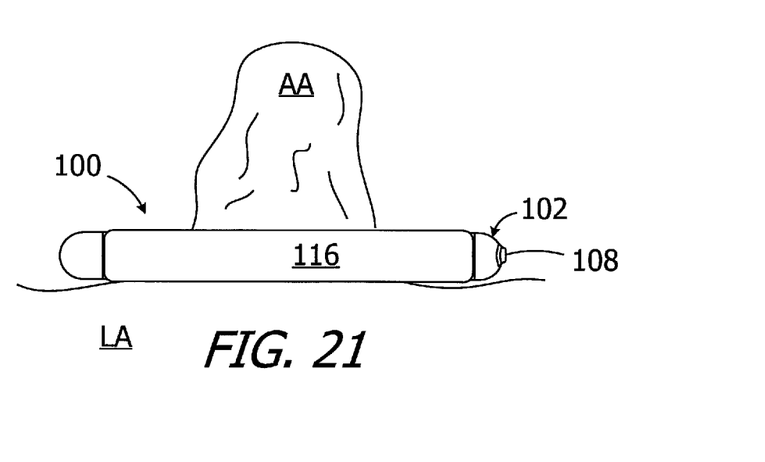
FIG. 21 is a side view of the inflatable atrial appendage occlusion apparatus illustrated in FIGS. 1-5 occluding an atrial appendage.

The inflation tool 210 may then be removed from the valve 108 by pulling the tube 212 proximally as illustrated in FIG. 20. As the valve 108 may be self-sealing, removal of the inflation tool 210 may cause the valve 108 to return to the closed state. The inflatable body 102 may, therefore, remain inflated and may continue to apply the compression pressure $P_C$ to the walls W and occlude the atrial appendage. The sutures 208 may also be disconnected by the deployment device 200 so that the deployment device 200 can be removed from the patient. The deployed occlusion device 100 may remain on the atrial appendage AA and epicardial surface indefinitely in the manner illustrated in FIG. 21. Should removal of the occlusion device 100 be required at a later date, the inflatable body 102 may be punctured and deflated to release the atrial appendage.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. A method, comprising the step of:
   occluding an atrial appendage by applying a compression pressure to the exterior surface of the atrial appendage with an inflatable apparatus including an inflatable body, defining an exterior and an interior volume that extends around a compression region, and a support member on the exterior of the inflatable body that is stiffer than the inflatable body, that is configured to prevent the inflatable body from bulging outwardly, that is movable between a collapsed state and an expanded state, and that is biased to the expanded state.

2. A method as claimed in claim 1, further comprising the step of:
   positioning the inflatable apparatus on and around the atrial appendage with the inflatable body in a deflated state.

3. A method as claimed in claim 1, wherein the inflatable apparatus includes a self-sealing valve, the method further comprising the step of:
   positioning the inflatable apparatus on and around the atrial appendage with the inflatable body in a deflated state and with a removable inflation tool located within the self-sealing valve.

4. A method as claimed in claim 3, further comprising the steps of:
   inflating the inflatable body; and
   after the inflating step, removing the inflation tool from the self-sealing valve.

5. A method as claimed in claim 1, further comprising the steps of:
   positioning the inflatable apparatus on and around the atrial appendage with the inflatable body in a deflated state; and
   inflating the inflatable body.

6. A method as claimed in claim 1, further comprising the step of:
   promoting tissue in-growth into a portion the inflatable apparatus.

7. A method as claimed in claim 1, further comprising the steps of:
   compressing the support member; and
   allowing the compressed support member to return to the expanded state to which it is biased.

8. A method as claimed in claim 1, wherein
   the inflatable body defines inner surfaces that face one another across a compression region in which the atrial appendage is located; and the support member is located on the inflatable body such that a plane passes through the compression region, the support member, and portions of the interior volume on opposite sides of the atrial appendage.

9. A method as claimed in claim 1, wherein
the inflatable body defines an outer perimeter; and
the support member extends around the outer perimeter.

10. A method as claimed in claim 1, wherein
prior to applying a compression pressure to the exterior surface of the atrial appendage, positioning the inflatable apparatus such that the inflatable body and the support member extend completely around the atrial appendage.

11. A method, comprising the step of:
occluding an atrial appendage by applying a compression pressure to the exterior surface of the atrial appendage with an inflatable apparatus including an inflatable body having first and second elongate linear hollow tubes and a pair of semi-circular hollow end tubes that connect the first and second elongate linear hollow tubes to one another such that an interior volume extends completely around the exterior surface of the atrial appendage.

12. A method as claimed in claim 11, further comprising the step of:
positioning the inflatable apparatus on and around the atrial appendage with the inflatable body in a deflated state.

13. A method as claimed in claim 11, wherein the inflatable apparatus includes a self-sealing valve, the method further comprising the step of:
positioning the inflatable apparatus on and around the atrial appendage with the inflatable body in a deflated state and with a removable inflation tool located within the self-sealing valve.

14. A method as claimed in claim 13, further comprising the steps of:
inflating the inflatable body; and
after the inflating step, removing the inflation tool from the self-sealing valve.

15. A method as claimed in claim 11, further comprising the steps of:
positioning the inflatable apparatus on and around the atrial appendage with the inflatable body in a deflated state; and
inflating the inflatable body.

16. A method as claimed in claim 11, further comprising the step of:
promoting tissue in-growth into a portion the inflatable apparatus.

17. A method as claimed in claim 11, further comprising the steps of:
compressing the inflatable apparatus; and
allowing the compressed inflatable apparatus to return to an expanded state to which it is biased.

18. A method as claimed in claim 11, wherein
the inflatable apparatus includes a support member that extends completely around the inflatable body, that is configured to prevent the inflatable body from bulging outwardly, that is movable between a collapsed state and an expanded state, and that is biased to the expanded state.

* * * * *